United States Patent [19]

Scheffler et al.

[11] Patent Number: 5,354,750
[45] Date of Patent: Oct. 11, 1994

[54] PHTHALAZINES CONTAINING AN AROMATIC ETHER OR THIOETHER GROUP IN THE 1-POSITION

[75] Inventors: Gerhard Scheffler, Bruchköbel; Ilona Fleischhauer, Offenbach; Bernhard Kutscher, Maintal; Jürgen Engel, Alzenau; Stefan Szelenyi, Schwaig; Ulrich Werner, Miehlen, all of Fed. Rep. of Germany

[73] Assignee: Asta Medica Aktiengesellschaft, Frankfurt, Fed. Rep. of Germany

[21] Appl. No.: 963,631

[22] Filed: Oct. 20, 1992

[30] Foreign Application Priority Data

Oct. 31, 1991 [DE] Fed. Rep. of Germany ....... 4135910

[51] Int. Cl.$^5$ .................... C07D 237/32; A61K 31/50
[52] U.S. Cl. ..................................... 514/248; 544/237
[58] Field of Search .......................... 544/237; 514/248

[56] References Cited

U.S. PATENT DOCUMENTS

| | | | |
|---|---|---|---|
| 2,484,029 | 10/1949 | Hartmann | 544/237 |
| 3,882,119 | 5/1975 | Nathansohn | 544/237 |
| 4,925,843 | 5/1990 | Takahashi | 544/237 |

OTHER PUBLICATIONS

Hayashi, Chem Abs 58, 3425 (1962).
Uoda, Chem Abs 88, 136646q (1977).

*Primary Examiner*—Mark L. Berch
*Attorney, Agent, or Firm*—Cushman, Darby & Cushman

[57] ABSTRACT

Pharmacologically active compounds of the General Formula

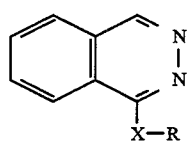

I where X is oxygen or sulphur and the radical R represents a quinuclidyl radical, an $C_1$-$C_6$-alkyl radical, a phenyl radical, a pyridyl radical, a phenyl or pyridyl radical substituted by the radicals $R_1$, $R_2$, and/or $R_3$, a $C_1$-$C_6$-alkyl radical substituted by pyridyl or alkylpyridyl or a $C_1$-$C_6$-alkyl radical substituted by phenyl, where each phenyl radical may also be substituted by the radicals $R_1$, $R_2$ and/or $R_3$ and the radicals $R_1$, $R_2$ and $R_3$ are the same or different and represent hydrogen, halogen, trihalogenmethyl, $C_1$-$C_6$-alkyl, $C_1$-$C_6$-alkoxy, carboxy, Carb-$C_1$-$C_6$-alkoxy, amino, $C_1$-$C_6$-alkylamino, $C_1$-$C_6$-dialkylamino, $C_1$-$C_6$-trialkylamino, $C_2$-$C_6$-alkanoylamino, or $C_2$-$C_6$-alkanoylamino which contains one more amino group in the alkyl portion, and their physiologically acceptable acid addition salts. The compounds provide analgesic, anti-inflammatory, anti-convulsive and anti-pyretic effects.

3 Claims, No Drawings

PHTHALAZINES CONTAINING AN AROMATIC ETHER OR THIOETHER GROUP IN THE 1-POSITION

The present invention relates to compounds which have a pronounced analgesic, anti-inflammatory, anticonvulsive and antipyretic effect.

BACKGROUND OF THE INVENTION

J. Prakt. Chemie 2, 51 (1895) page 148 and 149 describes the preparation of the compounds 1-methoxy-phthalazine and 1-ethoxy-phthalazine from 1-chlorophthalzaine and sodium methylate and sodium ethylate respectively.

U.S. Pat. No. 2,484,029 cites 1-phenoxy-phthalazine as starting substance for the preparation of 1-hydrazinophthalazine.

Neither of these references mentions that these compounds have pharmacological effects or renders these obvious.

SUMMARY OF THE INVENTION

An object of the present invention is to provide compounds with favorable pharmacological properties which may, for example, be utilized in analgesic and anti-inflammatory medications.

These and other objects are provided by compounds of the General Formula I:

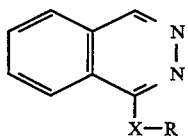

I where X is oxygen or sulphur and the radical R represents a quinuclidyl radical, an $C_1$-$C_6$-alkyl radical, a phenyl radical, a pyridyl radical, a phenyl or pyridyl radical substituted by the radicals $R_1$, $R_2$, and/or $R_3$, a $C_1$-$C_6$-alkyl radical substituted by pyridyl or alkylpyridyl or a $C_1$-$C_6$-alkyl radical substituted by phenyl, where each phenyl radical may also be substituted by tile radicals $R_1$, $R_2$ and/or $R_3$ and the radicals $R_1$, $R_2$ and $R_3$ are the same or different and represent hydrogen, halogen, trihalogenmethyl, $C_1$-$C_6$-alkyl, $C_1$-$C_6$-alkoxy, carboxy, Carb-$C_1$-$C_6$-alkoxy, amino, $C_1$-$C_6$-alkylamino, $C_1$-$C_6$-diaklylamino, $C_1$-$C_6$-trialkylamino, $C_2$-$C_6$-alkanoylamino or $C_2$-$C_6$-alkanoylamino which contains one more amino group in the alkyl portion, and their physiologically acceptable acid addition salts with the exception of 1-methoxy-phthalazine, 1-ethoxy-phthalazine and 1-phenoxy-phthalazine.

The compounds of the invention are pharmacologically active. In particular, the compounds of the invention have a pronounced and highly analgesic (for example peripheral analgesic, central analgesic), anti-inflammatory, anticonvulsive and antipyretic effect.

The following description contains important information by way of example:

The alkyl groups/alkyl radicals, alkoxy groups, alkanoyl amino groups or alkanoyl groups shown in Formula I may be straight or branched. The same also applies to alkyl and alkoxy groups if these are components of groups of different composition (for example in the form of a monoalkyl, dialkyl or trialkylamino group, alkanoylamino group or carbalkoxy group).

The alkyl and alkoxy groups as such or as components of groups of different compositions consist in particular of 1–4 carbon atoms, preferably 1 or 2 carbon atoms. Alkanoyl groups or alkanoylamino groups useful for the invention consist in particular of 2–4, preferably 2–3 carbon atoms. Alkylpyridyl represents a pyridyl radical containing one, two or also three $C_1$-$C_6$-alkyl radicals, preferably the methyl radical. The alkyl radicals are preferably in the 2-, 3-, 4- and/or 6-position of the pyridyl radical. The pyridyl radical itself is preferably connected via the 2-, 4- and/or 6-position to the $C_1$-$C_6$-alkyl radical. This also applies when the symbol R represents a pyridyl radical.

The $C_1$-$C_6$-alkyl radical substituted by pyridyl or alkylpyridyl is preferably a pyridylmethyl radical, that is a methyl radical preferably containing a pyridyl-(2)-, pyridyl-(4)- or pyridyl-(6)-radical where the pyridine ring may optionally also contain in addition one, two or three $C_1$-$C_6$-alkyl radicals, preferably methyl radicals.

The quinuclidine ring may preferably be the quinuclidyl-(3)-radical.

X preferably represents oxygen.

Compounds of Formula I where X is oxygen and R is phenyl or phenyl which contains an amino group or a $C_2$-$C_4$-alkanoylamino group, preferably in the 4-position have been found to be particularly effective.

Depending on the conditions of the process and on the starting materials, the compounds of Formula I are obtained in the free form or in the form of their salts. The salts of the compounds of Formula I (if these contain a basic nitrogen atom) may be converted in known manner into the bases, for example with alkali or ion exchangers. Salts may be obtained from the latter by reaction with organic acids, in particular those which are suitable for forming therapeutically usable salts.

The present invention also provides a process for the preparation of compounds of the General Formula I

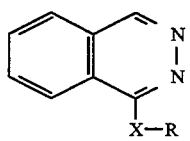

I where X is oxygen or sulphur and the radical R represents a quinuclidyl radical, a $C_1$-$C_6$-alkyl radical, a phenyl radical, a pyridyl radical, a phenyl or pyridyl radical substituted by the radicals $R_1$, $R_2$ and/or $R_3$, a $C_1$-$C_6$-alkyl radical substituted by pyridyl or alkylpyridyl or a $C_1$-$C_6$-alkyl radical substituted by phenyl, where each phenyl radical may also be substituted by the radicals $R_1$, $R_2$and/or $R_3$ and the radicals $R_1$, $R_2$ and $R_3$ are the same or different and represent hydrogen, halogen, trihalogenmethyl, $C_1$-$C_6$-alkyl, $C_1$-$C_6$-alkoxy, carboxy, Carb-$C_1$-$C_6$-alkoxy, amino, $C_1$-$C_6$-alkylamino, $C_1$-$C_6$-diaklylamino, $C_1$-$C_6$-trialkylamino, $C_2$-$C_6$-alkanoylamino or $C_2$-$C_6$-alkanoylamino which contains one more amino group in the alkyl portion, and their physiologically acceptable acid addition salts with the exception of 1-methoxy-phthalazine, 1-ethoxy-phthalazine and 1-phenoxy-phthalazine. In that process, a compound of the General Formula II:

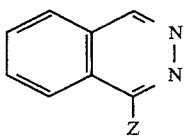

is reacted with a compound of the General Formula III:

R—Y     III where R has the meanings given above and Z is a halogen atom, if Y represents a hydroxy group, an $C_1$-$C_6$-alkylsulfonyloxy group or an arylsulfonyloxy group or a mercapto group, or Z is a hydroxy group or a mercapto group if Y represents halogen and optionally alkylating or acylating the compounds obtained and/or converting them into their acid salts.

The process for the preparation of compounds of Formulae II and III is carried out in a solvent or dispersing agent at temperatures between 20° and 200° C., preferably 30° and 150° C., in particular 40° and 80° C. Solvents or dispersing agents which may for example be considered are: lower aliphatic alcohols (1-6 carbon atoms such as propanol, isopropanol, butanol), lower aliphatic ethers (diethyl ether, diisopropyl ether), aromatic hydrocarbons (benzene, toluene, xylene), cyclic ethers (dioxane, tetrahydrofuran), esters of lower aliphatic carboxylic acids with lower aliphatic alcohols, amides and N-alkyl-substituted amides of aliphatic $C_1$-$C_4$-carboxylic acids (dimethyl formamide, dimethyl acetamide), $C_1$-$C_6$-dialkyl sulfones (dimethylsulfoxide) as well as other aprotic agents such as N-methyl pyrrolidone, tetramethyl urea, hexamethylphosphoric acid triamide, acetonitrile. The individual alkyl radicals of the above-mentioned solvents contain for example 1-6, in particular 1-4 carbon atoms.

The process is appropriately carried out in the presence of condensation agents. Condensation agents of this type that may for example be considered are: inorganic condensation agents such as alkali- or alkaline earth hydroxides, alkali hydrides, alkali amides, alkali carbonates or alkaline earth carbonates or organic bases such as pyridine, tertiary amines, piperidine, alkali alcoholates, alkali acetates or also triethyl phosphate. The alkali metals are in particular sodium or potassium. It is possible to work under phase transfer conditions (i.e. with the addition or one or several long-chain amines such as a benzyltributyl-ammonium-halide, a tetrabutyl-ammonium-halide or benzyl-triphenyl-phosphonium chloride.

One generally begins by first making the corresponding salt from the starting component that contains the hydroxy or mercapto group, using one of the above-mentioned alkali compounds and then reacting this with the second reaction component II.

If Y in Formula III is a $C_1$-$C_6$-alkyl-sulfonyloxy group, this is preferably one with 1-4 carbon atoms in the alkyl part (for example methylsulfonyloxy group). If Y in Formula III is an arylsulfonyloxy group, the aryl radical is preferably a phenyl or naphthyl radical, these optionally being substituted by $C_1$-$C_4$-alkyl radicals (in particular methyl radicals) (for example p-toluenesulfonyloxy group).

Preparation of starting substances of Formula II where Z=SH: compounds of this type may for example be obtained from compounds of Formula II where Z is a halogen atom (fluorine, chloride, bromide, iodine), by reaction with sodium- or potassium mercaptide in alcohols (methanol, ethanol, propylene glycol) at temperatures between 20° and 150° C. or also in aqueous medium at 100°-150° C. or through reaction with thiourea in lower alcohols (ethanol, isopropanol) at temperatures between 20° and 100° C. and subsequent alkaline decomposition (for example with aqueous sodium carbonate on a steam bath).

Another possibility is to heat compounds of Formula II, where Z is a hydroxy group, with phosphorus pentasulfide to temperatures between 50° and 200° C., for example 60°-160° C. These reactions may occur by analogy with the process described for example in Erwin Klingenberg, Pyridine and its Derivatives, Part IV (1964), pages 348-351 or in page 9 of DE-OS 2,230,392.

Starting materials of Formula III, where Y is the hydroxy group, may be obtained from compounds of Formula III where R is halogen by alkaline hydrolysis in a manner known per se, as described for example in C. Ferri, Reaktionen der organischen Synthese, 1978, page 200, or in Houben-Weyl, Methoden der organischen Chemie, vol. VI/1a, part 1, p. 180-191.

From compounds of Formula III, where Y is the hydroxy group, it is possible to obtain starting materials of Formula III where Y is a halogen atom, for example by reaction with thionyl halides (chlorides, bromides, iodides) or sulfonic acid chlorides in halogenated hydrocarbons (chloroform) or aromatic hydrocarbons (benzene) or in pyridine at temperatures between 20° and 150° C. (preferably boiling temperature of the solvent used). Starting materials of Formula III, where Y is an alkylsulfonyloxy group or an arylsulfonyloxy group, may for example be obtained from the corresponding hydroxy compounds (Y=OH) by reaction with $C_1$-$C_6$-alkylsulfonic acid chlorides or the corresponding arylsulfonic acid chlorides in the inert solvents conventionally used for that purpose (benzene, toluene, xylene, chloroform, methylene chloride, dioxane) at temperatures between 20°-150° C. The process is appropriately carried out in the presence of an acid-binding substance (for example tertiary amines such as triethylamine).

It is for example possible to obtain starting materials of Formula III where Y is the mercapto group from the halides of Formula III (Y=halogen) by reaction with alkali sulfides. These reactions may be carried out by analogy with C. Ferri, Reaktionen der organischen Synthese 1978, pages 205-209 or by analogy with for example page 9 of Published German Patent Application DE-OS 2,230,392.

Alkylation and Acylation

Reference is made to the acylation or alkylation of amino groups (for example when the radicals $R_1$, $R_2$ and/or $R_3$ represent amino- or monoalkylamino- or dialkylamino groups). The alkylation occurs for example by reaction with compounds of the Formula R'Hal, ArSO$_2$OR' and SO$_2$(OR'$_3$)$_2$, where Hal is a halogen atom (in particular chlorine, bromine or iodine) and Ar is an aromatic radical (for example a phenyl or naphthyl radical optionally substituted by one or several lower alkyl radicals) and R' is a $C_1$-$C_6$-alkyl group. Examples are p-toluenesulfonic acid-$C_1$-$C_6$-alkyl ester, $C_1$-$C_6$-dialkylsulfates, $C_1$-$C_6$-alkylhalides.

The alkylation and acylation reaction is optionally carried out with addition of conventional acid-binding agents such as alkali hydroxides, alkali carbonates, alkali hydrogen carbonates, alkaline earth carbonates, alkali acetates, tertiary amines (for example trialkylamine such as triethylamine), pyridine or also alkali hydrides at temperatures between 0° and 200° C., preferably 40° and 140° C. in inert solvents or suspension agents. Solvents or dispersing agents that may for example be considered are: aromatic hydrocarbons such as benzene, toluene, xylene; aliphatic ketones such as acetone, methylethyl ketone; halogenated hydrocarbons such as chloroform, carbon tetrachloride, chlorobenzene, methylene chloride; aliphatic ethers such as butyl ether; cyclic ethers such as tetrahydrofuran, dioxane; sulfoxides such as dimethylsulfoxide; tertiary acid amides such as dimethylformamide, N-methylpyrrolidone, hexamethylphosphoric acid triamide; aliphatic alcohols such as methanol, ethanol, isopropanol, amyl alcohol, tertiary butanol, cycloaliphatic hydrocarbons such as cyclohexane and the like. It is also possible to use aqueous mixtures of the solvents named. The process is often carried out at the reflux temperature of the solvent or dispersing agent used. The alkylation reaction components are often used in excess. The alkylation can also be carried out in the presence of tetraalkylammonium salts (in particular the halides) in combination with alkali hydroxides at temperatures between 0°–100° C., preferably 20°–80° C., in an aprotic solvent or also in chloroform or methylene chloride. Aprotic solvents that may in particular be considered are: tertiary amides (dimethylformamide, N-methyl-pyrrolidone, hexamethylphosphoric acid triamide) dimethylsulfoxide, acetonitrile, dimethoxyethane, acetone, tetrahydrofuran.

During the acylation, a $C_2$-$C_6$-alkanoyl group is for example introduced into compounds of Formula I which contain amino groups or NH groups.

This is carried out in a manner known per se preferably using Carb-$C_1$-$C_6$-alkoxyhalides (or the corresponding anhydrides) or using $C_2$-$C_6$-alkanoylhalides (or corresponding anhydrides). The reaction temperatures are preferably between 30° and 120° C.

It is also optionally possible to proceed during alkylation and acylation by first preparing an alkali compound (sodium-, potassium- or also lithium salt for example) of the compound to be alkylated or acylated by reacting it in an inert solvent such as dioxane, dimethyl formamide, benzene or toluene with an alkali metal, alkali hydride or alkali amide (in particular sodium or sodium compounds) or butyllithium at temperatures between 0° and 150° C. and then adding the alkylating or acylating agent.

Instead of the listed alkylating and acylating agents it is also possible to use other chemically equivalent agents conventionally used in chemistry (see for example also L. F. and Mary Fieser "Reagents for Organic Synthesis", John Wiley and Sons, Inc., New York, 1967, Vol. 1, pages 1303-4 and Vol. 2, page 471.

If the radical R in compounds of Formula I contains for example a Carb-$C_1$-$C_6$-alkoxy group or a $C_2$-$C_6$-alkanoyl group, these groups may be split off solvolytically. This splitting off is carried out in a known manner for example by saponification with acids (mineral acids such as hydrochloric acid, sulfuric acid, in particular concentrated hydrohalic acids such as HBr/glacial acetic acid) or using basic substances (potashes, soda, aqueous alkali solutions, alcoholic alkali solutions, aqueous $NH_3$) at temperatures between 10° and 150° C., in particular 20° to 100° C.

Those compounds of Formula I, which contain asymmetric carbon atoms and generally occur as racemates, may be split into the optically active isomers in a manner known per se, for example using an optically active acid. It is, however, also possible from the very beginning of the process to use an optically active starting material, a correspondingly optically active or diastereomeric form then being obtained as an end product.

The present invention also comprises the D- and L-forms as well as the DL-mixtures in the event that the compound of Formula I contains an asymmetric carbon atom and in the event of two or more asymmetric carbon atoms, as well as the corresponding diastereomeric forms.

The compounds of the invention are suitable for the preparation of pharmaceutical compositions. The pharmaceutical compositions or medications may contain one or several of the compounds of the invention. Conventional pharmaceutical carriers and auxiliary substances may be used to prepare the pharmaceutical formulations. The medications may for example be used enterally, parenterally (for example intravenously, intramuscularly, subcutaneously) or orally. Administration may for example be in the form of tablets, capsules, pills, coated tablets, suppositories or plasters: oily or aqueous solutions or suspensions (for example in sesame or olive oil), emulsions, injectable aqueous or oily solutions or suspensions. It is also possible, for example, to prepare dry ampoules which contain Compound I of the invention as active substance, the contents of dry ampoules of this kind being dissolved for example in water, physiological salt solution and dimethylsulfoxide, before use. The compounds of the invention display a good analgesic, anti-inflammatory and antipyretic effect, for example in the acetic acid writhing test, in the Randall-Selitto pain test and in the yeast fever test. A 50% inhibition of the writhing syndrome (characteristic stretching of the animals as a pain reaction) is for example achieved in the acetic acid writhing test at a dose of 5.6 mg/kg body weight mouse.

The minimum effective oral dose in the acetic acid writhing test is for example 3 mg/kg.

The general dosage range for the effect (animal experiments as set out above) that may for example be considered is:

5–30 mg/kg given orally or
3–20 mg/kg given intravenously.

The direction of effect of the compounds of the invention is comparable to the effect of the well-known pharmaceutically active substance paracetamol or acetylsalicylic acid although the following differences exist in particular: stronger and longer-acting effect, absence of gastrointestinal side effects. Indications for which the compounds of the invention may be considered are: pain, fever, epilepsy.

The pharmaceutical formulations generally contain between 25 and 500, preferably 100 to 250 mg of the active component(s) of the invention.

Manufacture may for example be in the form of tablets, capsules, pills, coated tablets, suppositories, ointments, gels, creams, powders, dusting powders, aerosols or in liquid form. Liquid forms of application which may for example be considered are: oily or alcoholic or aqueous solutions as well as suspensions and emulsions. Preferred forms of application are tablets containing between 100 and 250 mg or solutions containing between 1 and 10 percent by weight of active substance.

The single dose of the active component of the invention may for example be a) in oral medicinal forms, between 50 and 400 mg, preferably 100–250 mg
b) in parenteral medicinal forms (for example intravenous, intramuscular), between 25 and 250 mg, preferably 50–125 mg
c) in medicinal forms for inhalation (solutions or aerosols), between 1 and 10%, preferably 2–5%
d) in medicinal forms for rectal or vaginal application, between 50 and 500 mg, preferably 125–500
e) in medicinal forms for local application to the skin and mucous membranes (for example in the form of solutions, lotions, emulsions, ointments and the like), between 1 and 10%, preferably 2–5%

(The doses are in each case based on the free base. If salts are used the amount must be adjusted appropriately)

It is for example possible to recommend 3 times daily 1 to 2 tablets containing 50 to 250 mg active substance or for example in the case of intravenous injection 1 to 2 times daily one ampoule of 3 to 5 ml content with 25 to 250 mg substance. In oral administration the minimum daily dose is for example 150 mg; the maximum daily dose in oral administration should not exceed 1500 mg.

The acute toxicity of the compounds of the invention in the mouse (expressed by the $LD_{50}$ mg/kg method after Miller and Tainter: Proc. Soc. Exper. Bio. a. Med. 57 (1944) 261) is for example over 600 mg/kg per os in the case of oral application.

The medications may be used in human medicine, in veterinary medicine and in agriculture, alone or mixed with other pharmacologically active substances.

DETAILED DESCRIPTION OF PREFERRED EMBODIMENTS

The following Examples serve to illustrate the invention

EXAMPLES

General instructions for preparing Examples 1–15 according to Table 1:

0.30 mol of compound III are dissolved in 100 ml dimethylacetamide (abbreviated DMA) and added dropwise to a suspension of 0.33 mol sodium hydride in 70 ml DMA under cooling (iced water). The apparatus is previously rinsed with argon. When the exothermic reaction is complete (1.5–2 hours), a solution of 0.30 mol 1-chlorophthalazine (95%) in 230 DMA is added dropwise at 20° to 40° C. for two hours. The reaction mixture is then stirred for about 5 hours at a bath temperature of 40°–80° C.

After completion of the reaction about 50 ml water are added dropwise to the reaction mixture with ice cooling and then evaporated in a rotatary evaporator in a water jet vacuum at room temperature to a volume of about 150 ml. The reaction mixture concentrated in this manner is then poured with vigorous stirring into 1 liter of iced water. The precipitated reaction product is suction filtered and washed with water and then optionally with petroleum ether.

The raw product obtained in this manner is recrystallized in the conventional manner, optionally with addition of active charcoal and/or kieselguhr.

The compounds prepared are listed in Table 1. In the compounds according to Examples 1 to 14, X is oxygen in each case. In Example 15, X =sulphur.

| Example No. | R | Melting Point | Recrystallized Form | Yield |
|---|---|---|---|---|
| 1 | $C_6H_5-$ | 105–106° C. | 2-propanol | |
| 2 | $4\text{-}CH_3O\text{-}C_6H_4-$ | 149–151° C. | Ethanol | |
| 3 | $4\text{-}NH_2\text{-}C_6H_4-$ | 195–196° C. | Ethanol | |
| 4 | $4\text{-}CH_3\text{-}CO\text{-}NH\text{-}C_6H_4-$ | 213° C. | Ethanol | |
| 5 | $3\text{-}CH_3\text{-}CO\text{-}NH\text{-}C_6H_4-$ | 232–234° C. | Ethanol | |
| 6 | $C_2H_5-$ | 57° C. | Petroleum Ether | |
| 7 | $2,3,4,\text{-}(CH_3O)_3\text{-}C_6H_2-$ | 183° C. | Ethanol | |
| 8 | $C_6H_5\text{-}CH_2-$ | brown liquid | Cleaned using column chromatography | |
| 9 | $4\text{-}CH_3O\text{-}CO\text{-}C_6H_4-$ | 168–169° C. | Methanol | |
| 10 | $4\text{-}(NH_2\text{-}CH_2\text{-}CO\text{-}NH)\text{-}C_6H_4-$ | >248° C. (disint.) Hydrochloride | Salt formation in MeOH with HCl/2 propanol | |
| 11 | 2-Pyridyl-$CH_2-$ (2-Picolyl-) | 99–102° C. (base) 114–115° C. (maleate) | DMA/water[1] Salt formation of the maleate in acetone with maleic acid/acetone | |
| 12 | 4-Pyridyl-$CH_2-$ (4-Picolyl-) | 134–135° C. | DMA/water[1] | |
| 13 | 1-Aza-bicyclo 2,2,2- octan-3-yl- (3-quinuclidyl) | 230–231° C. Hydrochloride | Salt formation in 2-propanol with HCl/2-propanol | |
| 14 | $4\text{-}F\text{-}C_6H_4$ | 141–144° C. | 2-Propanol | |
| 15 | $C_6H_5(X = S)$ | 129–132° C. | DMA/water[1] | |

What is claimed is:
1. Compounds of the Formula I

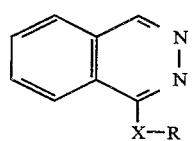

where X is oxygen and the radical R represents a quinuclidyl radical, a phenyl radical, a pyridyl radical, a phenyl or pyridyl radical substituted by the radicals $R_1$, $R_2$ and/or $R_3$, a $C_1$-$C_6$-alkyl radical substituted by pyridyl or alkylpyridyl or a $C_1$-$C_6$-alkyl radical substituted by phenyl, where each phenyl radical may also be substituted by the radicals $R_1$, $R_2$ and/or $R_3$ and the radials $R_1$, $R_2$ and $R_3$ are the same or different and represent hydrogen, halogen, trihalogenmethyl, $C_1$-$C_6$-alkyl, $C_1$-$C_6$-alkoxy, carboxy, Carb-$C_1$-$C_6$-alkoxy, amino, $C_1$-$C_6$-alkylamino, $C_1$-$C_6$-dialkylamino, $C_2$-$C_6$-alkanoylamino or $C_2$-$C_6$-alkanoylamino which contains one or more amino groups in the alkyl portion, and their physiologically acceptable acid addition salts with the exception of 1-methoxy-phthalazine, 1-ethoxy-phthalazine and 1-phenoxy-phthalazine.

2. A pharmaceutical composition for producing analgesia, or antiinflammatory, anticonvulsive and/or antipyretic effects comprising an effective amount of a compound of the Formula I

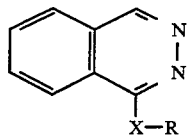

where X is oxygen or sulphur and the radical R represents a quinuclidyl radical, a $C_1$-$C_6$-alkyl radical, a phenyl radical, a pyridyl radical, a phenyl or pyridyl radical substituted by the radicals $R_1$, $R_2$ and/or $R_3$, a $C_1$-$C_6$-alkyl radical substituted by pyridyl or alkylpyridyl or a $C_1$-$C_6$-alkyl radical substituted by phenyl, where each phenyl radical may also be substituted by the radicals $R_1$, $R_2$ and/or $R_3$ and the radials $R_1$, $R_2$ and $R_3$ are the same or different and represent hydrogen, halogen, trihalogerunethyl, $C_1$-$C_6$-alkyl, $C_1$-$C_6$-alkoxy, carboxy, Carb-$C_1$-$C_6$-alkoxy, amino, $C_1$-$C_6$-alkylamino, $C_1$-$C_6$-dialkylamino, $C_2$-$C_6$-alkanoylamino or $C_2$-$C_6$-alkanoylamino which contains one or more amino groups in the alkyl portion, and their physiologically acceptable acid addition salts with the exception of 1-methoxy-phthalazine, 1-ethoxy-phthalazine and 1-phenoxy-phthalazine and a pharmaceutically acceptable carrier or diluent therefor.

3. A method of producing analgesic, anti-inflammatory, anticonvulsive or antipyretic effects in a patient in need thereof which comprises administering an effective amount of a compound of the Formula I

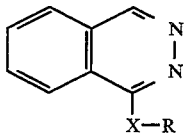

where X is oxygen or sulphur and the radical R represents a quinuclidyl radical, a $C_1$-$C_6$-alkyl radical, a phenyl radical, a pyridyl radical, a phenyl or pyridyl radical substituted by the radicals $R_1$, $R_2$ and/or $R_3$, a $C_1$-$C_6$-alkyl radical substituted by pyridyl or alkylpyridyl or a $C_1$-$C_6$-alkyl radical substituted by phenyl, where each phenyl radical may also be substituted by the radicals $R_1$, $R_2$ and/or $R_3$ and the radials $R_1$, $R_2$ and $R_3$ are the same or different and represent hydrogen, halogen, trihalogenmethyl, $C_1$-$C_6$-alkyl, $C_1$-$C_6$-alkoxy, carboxy, Carb-$C_1$-$C_6$-alkoxy, amino, $C_1$-$C_6$-alkylamino, $C_1$-$C_6$-dialkylamino, $C_2$-$C_6$-alkanoylamino or $C_2$-$C_6$-alkanoylamino which contains one or more amino groups in the alkyl portion, and their physiologically acceptable acid addition salts with the exception of 1-methoxy-phthalazine, 1-ethoxy-phthalazine and 1-phenoxyphthalazine.

* * * * *